(12) United States Patent
Goldstein

(10) Patent No.: US 8,973,585 B2
(45) Date of Patent: Mar. 10, 2015

(54) LABORATORY APPARATUS

(76) Inventor: David Goldstein, Porltand, OR (US)

( * ) Notice: Subject to any disclaimer, the term of this patent is extended or adjusted under 35 U.S.C. 154(b) by 679 days.

(21) Appl. No.: 13/285,177

(22) Filed: Oct. 31, 2011

(65) Prior Publication Data

US 2013/0104738 A1 May 2, 2013

(51) Int. Cl.
| | |
|---|---|
| *A24F 1/30* | (2006.01) |
| *B01D 53/14* | (2006.01) |
| *B01D 46/10* | (2006.01) |
| *B01D 47/02* | (2006.01) |
| *B01D 50/00* | (2006.01) |
| *B01L 5/04* | (2006.01) |

(52) U.S. Cl.
CPC ............... *B01D 53/14* (2013.01); *B01D 46/10* (2013.01); *B01D 47/021* (2013.01); *B01D 50/004* (2013.01); *B01D 2221/10* (2013.01); *B01L 5/04* (2013.01); *B01L 2300/0681* (2013.01); *B01L 2400/049* (2013.01)
USPC ................ 131/173; 131/331; 95/214; 96/361

(58) Field of Classification Search
CPC ............... A24F 1/00; A24F 1/02; A24F 1/04; A24F 1/06; A24F 1/08; A24F 1/10; A24F 1/16; A24F 1/30
USPC .......................................................... 131/173
See application file for complete search history.

(56) References Cited

U.S. PATENT DOCUMENTS

| | | | | |
|---|---|---|---|---|
| 2,487,539 | A | | 10/1949 | Johnstone |
| 3,882,875 | A | * | 5/1975 | Frost ............................ 131/173 |
| 3,986,851 | A | * | 10/1976 | Grodek ......................... 55/488 |
| 4,014,353 | A | * | 3/1977 | Kahler .......................... 131/173 |
| 4,031,905 | A | * | 6/1977 | Dunn ............................ 131/173 |
| 4,148,327 | A | * | 4/1979 | Graham ........................ 131/173 |
| 4,164,950 | A | * | 8/1979 | Bechtold ...................... 131/194 |
| 4,363,639 | A | | 12/1982 | Gladon |
| 6,067,993 | A | * | 5/2000 | Mahoney, III ................ 131/173 |
| 6,250,301 | B1 | * | 6/2001 | Pate ........................ 128/203.26 |
| 2004/0163658 | A1 | * | 8/2004 | Mehio ........................... 131/191 |
| 2011/0094524 | A1 | * | 4/2011 | Glover ......................... 131/224 |

FOREIGN PATENT DOCUMENTS

| | | | |
|---|---|---|---|
| CH | 690316 | * | 7/2000 |
| DE | 19621340 | * | 2/1998 |

* cited by examiner

*Primary Examiner* — Richard Crispino
*Assistant Examiner* — Eric Yaary
(74) *Attorney, Agent, or Firm* — Peter A. Haas Esquire LLC

(57) ABSTRACT

The present invention relates to a glass laboratory apparatus that includes a pre filter and a main filter to scrub solids from a gas using water filtration. A preferred embodiment of the present invention includes a main vessel adapted to hold a volume of a liquid such as water and an inlet conduit with an opening above the liquid level in the main vessel and an outlet below the surface of the liquid level in the main vessel. A pre filter arranges in the inlet conduit at a level above the liquid level in the main vessel. A main filter is located below the water level in the main vessel. A negative pressure is supplied to draw a gas through the first, pre-filter, through the water and second main filter.

1 Claim, 4 Drawing Sheets

LABORATORY APPARATUS

BACKGROUND

The present invention relates to laboratory glassware and more specifically to a dual-filtering apparatus using at least one fritted disc and a pre-filter to filter out solid particles, precipitate, or residue from a gaseous substance.

Laboratory glassware generally refers to a variety of devices, traditionally made of glass, suitable for scientific experiments and other work in science, particularly for use in chemistry and biology laboratories. Glass is often preferred in such environments because it is relatively inert, transparent, heat-resistant, and relatively easy to configure as needed for a particular experiment or application. Borosilicate laboratory glass-often sold under the trade name "Pyrex," is commonly utilized as its chemical inertness, transparency, and resistance to thermal stress make it the ideal material for most wet chemistry reactions.

Other types of glass are known in this art. For example, in some applications quartz glass is used: it can withstand high temperatures and offers transparency in certain parts of the electromagnetic spectrum. In other applications, especially some storage bottles, darkened brown or amber (actinic) glass is used to keep out much of the UV and IR radiation so that the effect of light on the contents is minimized. Heavy-wall glass is used for pressure reactors.

One particularly specialized use of glass in the laboratory includes glass as a filter device. Such a glass filter, termed fritted glass, is finely porous glass mass through which gas or liquid may pass. It is made by sintering together glass particles into a solid but porous body. This porous glass body can be called a frit. Applications in laboratory glassware include use in fritted glass filter items, scrubbers, or spargers. Other laboratory applications of fritted glass include packing in chromatography columns and resin beds for special chemical synthesis.

In a fritted glass filter, a disc or pane of fritted glass is used to filter out solid particles, precipitate, or residue from a fluid (or gas), which passes through the pores in the fritted glass. In the case of a gas, a pressure difference is often required to either push or draw the gas through the fritted filter. The liquid or gas passes through the fritted filter, but any solid (larger than the porosity of the frit) will be prevented from flowing through the frit.

Fritted glass is manufactured from individual bead or particles of glass fused, or sintered, into a solid, but porous glass body. Fritted discs are made by heating glass particles or fibers at a high enough temperature that they fuse together sufficiently that they become a relatively strong mass with a desired porosity. For example, a borosilicate glass frit can be made from particulate glass or from short pieces of fiber.

The porosity of a frit is related to the mesh range of the glass beads (particles) or fibers. The mesh range of glass beads or packing determines a nominal particle size: For example, a 200-400 mesh corresponds to 37-74 µm, and are sometimes called out as 40 µm. This means that a frit with a pore size of 16-40 µm will not clog when used to support a nominal 40 µm packing. Commonly, a frit may be classified as a medium porosity frit having 10-15-µm porosity, a coarse porosity frit having a 40-60 µm porosity, or an extra-coarse porosity frit having a 170-220 µm porosity.

A single fritted filter is a common part of laboratory glassware and such items as fritted glass funnels and fritted glass crucibles are generally known and available in this art. Such single-fritted-filter device include a laboratory scale sparger (also known as gas diffusing stones or diffusors), a scrubber, and a gas-washing bottle (or Drechsel bottle). Such devices include a fritted glass piece fused to the tip of a gas-inlet tube. This fritted glass tip is placed inside the vessel with liquid inside during use such that the fritted tip is submerged in the liquid. To maximize surface area contact of the gas to the liquid, a gas stream is slowly blown into the vessel through the fritted glass tip so that it breaks up the gas into many tiny bubbles. The purpose of sparging is to saturate the enclosed liquid with the gas, often to displace another gaseous component. The purpose of a scrubber or gas-washing bottle is to scrub the gas such that the liquid absorbs one (or more) of the gaseous components to remove it from the gas stream, effectively purifying the gas stream.

One exemplary single fritted filter laboratory glassware, described by Johnstone in U.S. patent application Ser. No. 248,739 issued on 25 Oct. 1949, includes two chambers, one being placed within the other so that there is an annular space between the two chambers. A single fritted disc locates in the inner chamber to scrub a gas as it enters the chamber. Another example of single fritted disc filter includes the device of U.S. Pat. No. 4,363,639 to Gladon issued on 14 Dec. 1982.

Despite the benefits of a single stage (one fritted disc) filtration device, there remains a need for an apparatus having two fritted discs, or at least one fritted disk in line with a pre-filter, or preferably a serviceable, removable pre-filter which may be a fritted glass disc or other incombustible porous medium in line with the main fritted filter disc. A dual filtration device better enables scrubbing gas from a direct combustion process, which results in solid combustion byproducts, either burned to ash or incompletely so. Separating the solids from the gas prior to filtration has two primary benefits: (1) Dry recovery of combusted or heated materials, which allows for further analysis of post process materials; and (B) Dry recovery, which prevents contamination of main filter surface by particulates and resins.

SUMMARY OF THE INVENTION

The U.S. Surgeon General's report on water pipes for tobacco use in 1963 suggested that there may be beneficial reduction of harmful constituents in tobacco smoke by water filtration: Accordingly, one use of the present invention includes the filtration of tobacco smoke. And, laboratory analysis conclusively demonstrate the benefits of water filtration for consuming tobacco by comparing water-filtered smoke versus more traditional methods of ingestion. This device is well suited to that task. Prior art has no provision for introduction of freshly produced combustion or volatilized gas into a fritted filter at the modest static pressures, as typically applied when used to smoke tobacco.

The Surgeon General's suggestion indicates the need for more definitive analysis. The apparatus of the present invention is designed and intended to provide definitive laboratory analysis as to the efficacy of water filtering tobacco smoke as a means of toxics reduction versus more traditional methods of ingestion. This device is well suited to this important task.

Moreover, consumer demand has anecdotally proven the value of water filtration and consumers are demanding more efficient water filtering combustion devices. Some of these newer designs have evolved into considerably more intricate forms, incorporating elements of laboratory glass fabrication into their design. Some of these designs are improvements over traditional designs dating back into the 1970's. None are well suited to actual laboratory use.

This product has widespread commercial potential as well as scientific merit because it can be used to remove volatile solids from a gas by passing the gas through a water and fritted disc filtering system wherein the aperture size determined in the manufacturing of the fritted disc determines the maximum particle size remaining suspended in an effluent stream. Further, a pre-filter is used to increase the efficiency of the main filter.

DRAWING

DESCRIPTION OF THE INVENTION

Figure 1:
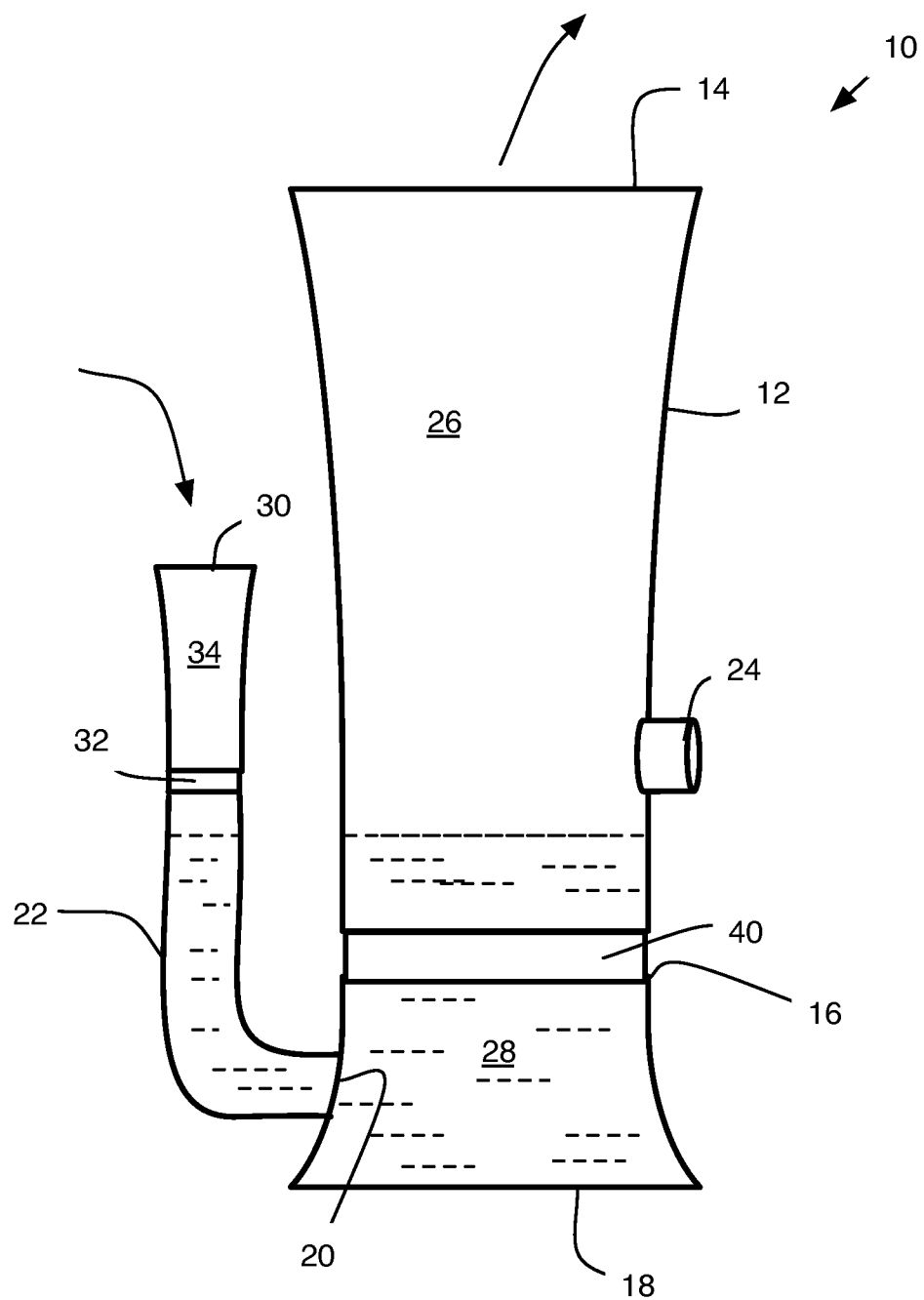
FIG. 1 is a side view of a laboratory glass apparatus according to a preferred embodiment of the present invention.

Possible preferred embodiments will now be described with reference to the drawings and those skilled in the art will understand that alternative configurations and combinations of components may be substituted without subtracting from the invention. Also, in some figures certain components are omitted to more clearly illustrate the invention.

In one preferred embodiment, the present invention contemplates a glass laboratory apparatus filtration device having two filters. A pre-filter, which is preferably a fritted disk, although a stainless-steel mesh screen would work equally well or a carbon fiber filter or an activated charcoal filter or other similar pre-filtering device, and a second fritted disc. The apparatus 10 includes a sample vessel 12 having an open top 14 supported by one or more sidewalls, a ledge or other similar means 16 for supporting a (second) fritted disc 40 and a bottom surface 18 having an aperture 20 connected to a downward directed conduit 22. The vessel 12 defines a chamber having a bottom and at least one sidewall with an open top and the chamber 26 is well suited for holding a liquid 28 such as water. The vessel optionally includes a relief valve 24 for selective evacuation of gas from the chamber.

In one contemplated embodiment the prefilter is a demountable, supported prefilter, which is confined to the narrow end of standard inner (male) taper ground by a close fitting outer (female) standard taper joint. Preferably, the prefilter is standardized at 15-mm to sit on $^{19}/_{25}$-inch inner S/T joint snugly.

In other contemplated embodiments, the first fritted disc may be substituted with any pre-filter device including a porous, incombustible pre-filter and can be configured in the vessel, for example by inverting a cone of an upturned standard-taper inner joint to form a support shelf for aforementioned pre-filter.

Figure 2:
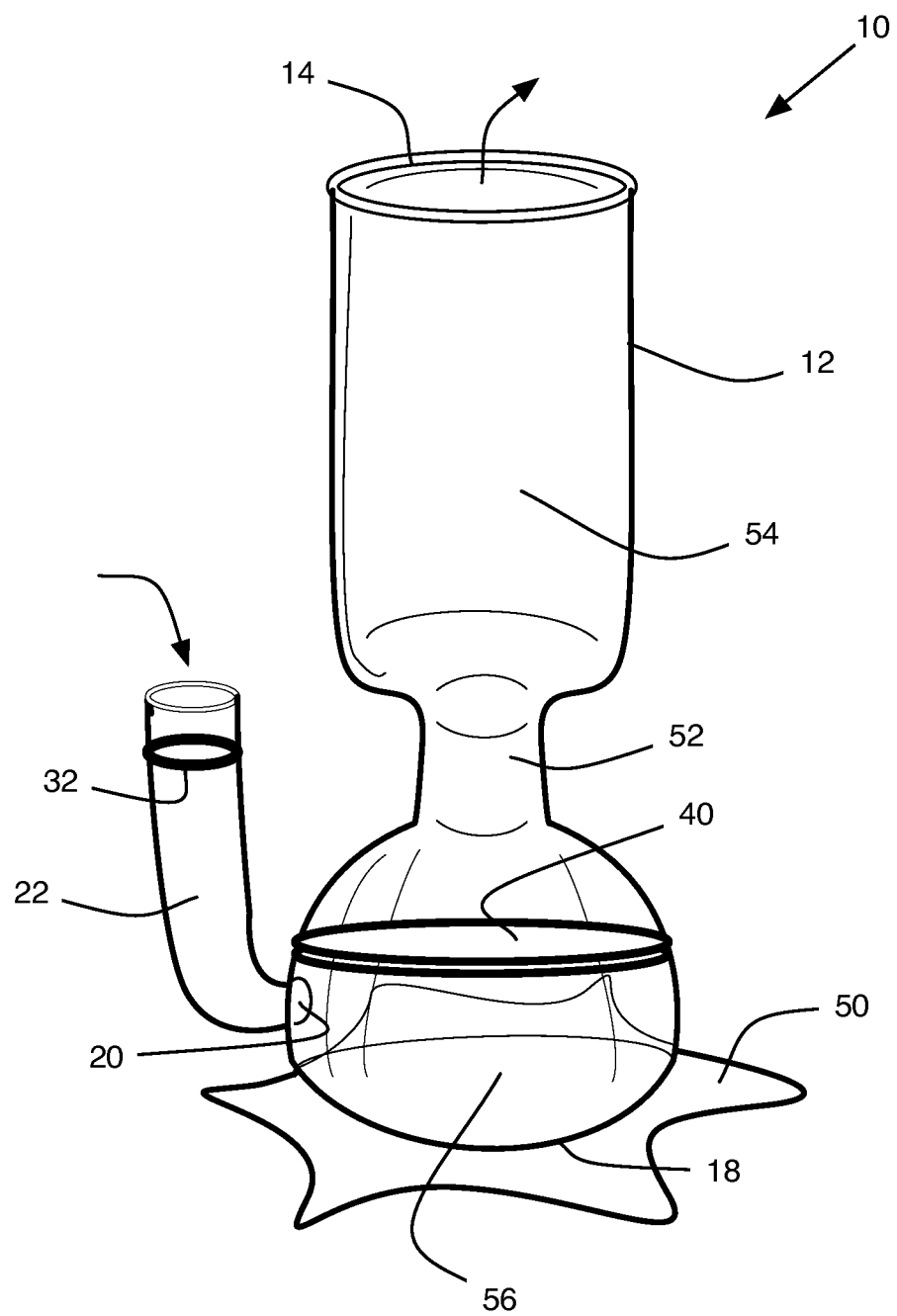
FIG. 2 is an offset frontal view of an alternative embodiment of the present invention.

As FIG. 2 illustrates, the vessel, further may include an ice shelf 52, a narrowing of the vessel's vertical sidewall to retain an ice cube or block of ice to further cool the effluent gas after the gas has exited the main filter fritted disc and has already passed out of the liquid. The ice block further cools the gaseous sample and further condenses out volatile solids that my have escaped the fluid and fritted disc. Further, the restriction of the ice shelf 52 divides the vessel into an upper chamber 54 and a lower chamber or bowl 56. The second fritted disc 40 arranges in the second, lower chamber 56 and the level of the fluid covers the filter 40 but is at a level that is below the ice shelf 52 and below the pre-filter 32.

The downward directed conduit 22, in turn, links the sample vessel 12. Specifically, the downward directed tube terminates in an opening in a sidewall 20 of the apparatus body, and this aperture is near the bottom, adjacent to a bottom wall of the main body of the apparatus. The conduit 22 has an inlet opening 30 near the top. A first fritted disc 32 fits near the open top. An inlet chamber 34 hermetically seals to the first fritted disc or other pre-filter including a stainless steel mesh or carbon fiber or other similar filter device, which is positioned such that the solution or liquid 28 rests at a level that is below the first fritted disc or pre-filter 32.

A fluid, or more precisely, a gas conduit is formed by the linking or coupling from the inlet opening 30 to the exhaust opening 14. Thus, when a pressure differentiation is affected (lower pressure at the exhaust) a gas is forced through the first fritted disc or pre filter 32 through the liquid solution 28 and up through the second disc 40.

The inlet chamber 34 includes means for burning a sample. As such, the apparatus of the present invention is well-suited for scrubbing a gas of undesired particles, solids, and other impurities. Another benefit, if used with water in the main chamber, is the cooling effect of the water and that the water can trap some heavier particles and water-soluble molecules, preventing them from entering the effluent stream.

In the preferred embodiments, the first or pre-filter should be kept dry, and therefore it must be above the water level in the vessel. This is important because it becomes immediately clogged if wet. Alternatively, a check valve may be included to keep the pre-filter dry regardless of the water level in the vessel. The orifice of the gas-generating portion (bowl) must be sufficiently wide to allow for adequate airflow: One suitable interior diameter of such an orifice is about 6-mm. The bowl may be heated by hot air or open flame. In the case of combustion, the burning material will usually suck down through the combustion venturi orifice before it has entirely burned.

Now, regarding the combustion or vaporization of the sample, a funnel terminating in a restricted orifice of approximately 6-mm is provided so that volume of airflow is not compromised by excessive static pressure while the sample is contained in a configuration promoting efficient combustion. This combustion gas generator is affixed to the body of the apparatus in an airtight fashion by means of a standard taper ground joint, in this case either $^{19}/_{22}$-mm or $^{19}/_{26}$-mm standard taper joint. This configuration also serves to position the pre-filter precisely on the inner joint, which supports it. The combustion/vapor generator may be made from borosilicate or quartz materials. Quartz allows for more heating options and increased durability.

The apparatus of the present invention is well-suited for scrubbing a gas of undesired particles, solids, and other impurities. Another benefit, if used with water in the main chamber, is the cooling effect of the water and that the water can trap some heavier particles and water-soluble molecules, preventing them from entering the effluent stream.

One use of the present invention includes filtering smoke, such as tobacco. A sample of burning tobacco is placed in the inlet chamber 34 and ordinary water is placed in the vessel as the liquid 28—this is known as water filtration and there is substantial epidemiological evidence of lower incidences of carcinoma among tobacco smokers using water filtration compared to other methods of inhaling tobacco products—i.e. from a cigarette, pipe, or cigar. The gas-dispersion frit serves to break up the smoke into very fine bubbles, thereby increasing its water-contact area. Frits are commonly referred to as "diffusers" for the way that they diffuse (or disperse) the particulates suspended in the gas as it exits the vessel.

The present invention can be altered physically to affect the needed pressure differential to cause bubble filtration through the two filters. The greater the volume of water, the greater the pressure differentiation required to scrub the gas. The defined range of pressure differential is limited by water column height, which should not exceed the height of the pre-filter, as it works poorly when wet. Additionally, allowing the combusted remains to get wet would create recovery and purity issues for the research chemist.

In one suitable preferred embodiment, a laboratory apparatus 10 consists of blown glass, specifically the apparatus is fabricated from borosilicate glass tubing, 33-expansion type and includes two filters, preferably a first (pre-filter) fritted disc and second fritted disc, however the pre-filter could also be a stainless steel mesh screen or any incombustible yet porous substance, as would be appreciated by those skilled in this art. Each disc is fabricated by filling rings of high-temperature fused silica (quartz) glass with commercially available clear borosilicate frit, large size (#25 mesh) as supplied, for example by North Star Glass and/or Glass Alchemy (both located in Portland, Oreg., USA).

Alternatively, a fritted disc consists of a mullite shelf that has been core-drilled to mold size, or the fritted discs may be fused in a ceramic mold that has been perforated (by core drill) with a grid of properly sized holes to mass produce many fritted discs in a single firing, then coated with alumina-kaolin mold release, which is dried before being loaded with loose frit. This process is a faster and more economical process that is better suited to larger production quantities. Further, the plugs cut from the mullite plate will make good weights to ensure both sides of the disc are flat, for example. In other embodiments, known methods and materials for refractory type glass would also work and are contemplated in the scope of the invention.

Then, the quartz rings are placed on a mullite kiln shelf lined with ceramic kiln fusing paper on the bottom or a mold release is used, filled them with frit, and kiln fired them up to about 1550-degrees F. for about 40 minutes. Once cool, the result is a highly porous fritted disc with little resistance to flow of gas or liquid.

To avoid significant breakage of the fritted discs, a kiln wash/glass release using kaolin clay and alumina hydrate is painted the slurry on the quartz rings, dried it out, and then filled the rings with frit. Moreover, a glass release compound of kaolin clay and alumina hydrate slurry is applied to all mold surfaces to prevent damage to both molds and fritted ware upon release, as would be well understood by those skilled in this art.

The discs 32 and 40 can be made in small batches or, alternatively, for larger production quantities, fabricating the fritted discs—instead of quartz rings that need to be filled individually—from flat plate stock that has been core-drilled to the proper diameter so that many mold orifices can be filled quickly from bulk, and the leftover slug from core drilling can be used as a weight to make both sides of the disc even and parallel. Further economies can be gained from using a kiln wash as an effective substitute for more expensive and time consuming kiln paper covering the mullite kiln shelf.

In other embodiments, mullite—instead of quartz—can be used for a mold material. It is a bit cheaper (both are expensive), but easier and faster to drill holes in. Graphite would also work, but graphite oxidizes at fusing temperature, which would distort mold dimensions and be consumed without a nitrogen or inert gas atmosphere.

FIG. 2 shows a base 50 connected or fused to the vessel at a lower portion. The base aids in supporting the vessel on a level surface and, accordingly can be any shape. One contemplated shape is a hexagonal base, another contemplated shape is a six-pointed concave hexagon with curved line segments joining each adjacent point of the six points, each point equally distant from the bases geometric center; although those skilled in the art would appreciate that additional configurations for the base would work equally well. Not shown in the drawings, but contemplated nevertheless: A supporting member adapts to connect the inlet portion to the main body of the vessel, this supporting member is not in fluid connection with the inlet and outlet, but serves merely to mechanically strengthen and reduce the propensity for damage and breakage of the inlet tube portion relative to the main vessel body.

Also, in an alternative contemplated embodiment, the vessel ideally has one common outer diameter. Thus, ice shelf or restriction of the inner diameter of the vessel can be shaped during the formation of the vessel, for example it can be formed from a massive thickening of the original tube, then blown against a flat carbon paddle. This way, the OD is unchanged but the ID is restricted.

Other contemplated modifications to the present invention include accessories for glass water pipes in general. Those skilled in the art could readily adapt such known accessories to work with the present invention as shown and described herein.

The use of standard taper ground joints will allow for a variety of commercially available accessories to be used in conjunction with this product. Botanical essences can be vaporized most efficiently by means of the sheathed quartz cup as pictured in the accompanying figures of the drawing.

Other enhancements to the present invention is using three or more filters in various arrangements. Further, the vessel may be made of quartz for improved durability.

Other modifications contemplated with any of the preferred embodiments include a dome structure that acts as a chimney and prevents or restricts the rate of vapor escaping—an example of this is captured in FIG. 2 wherein a narrowed opening above the water chamber acts as the chimney.

Figure 3:
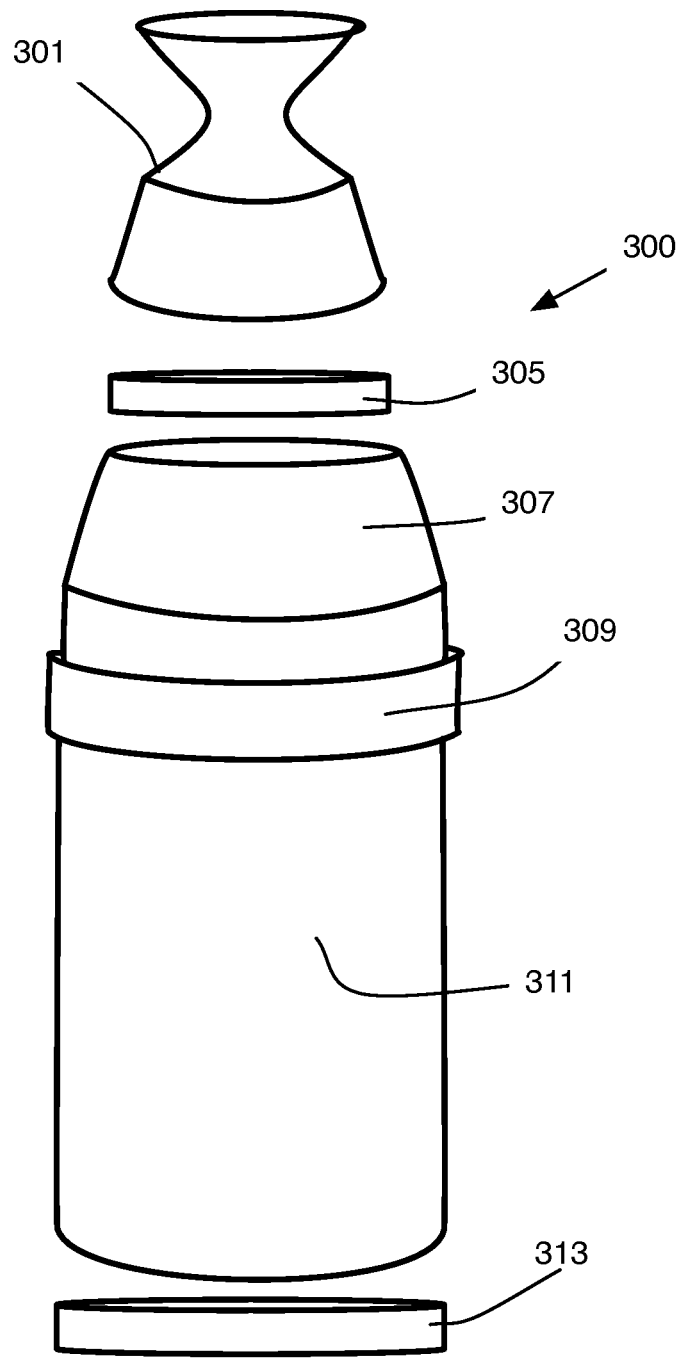
FIG. 3 is an exploded front view of a filter insert adapted to retrofit standard glassware of the prior art.

FIG. 3 shows an insert 300 adapted to fit inside the inlet chamber of glassware already known in the art and, accordingly, retrofits prior-art glassware to have a pre-filter fritted disc and a main filter fritted disc. This insert 300 fits over a standard taper and inserts under a standard chamber piece 301. The insert 300 includes a pre filter element 305, which is held in place in the tapered portion by a snug fitting rod assembly having a tapered nose 307 and cylindrical shaft portion 311. A rubber washer, o-ring or other similar stopper-type sleeve 309 fits on the shaft to snug the shaft into the vapor cup. A second pre-filter fritted disc 313 arranges at the opposite end of the shaft and fits in the inlet chamber 34 as described above, and, ideally, is fused to the bottom of the lower shaft 311.

Figure 4:
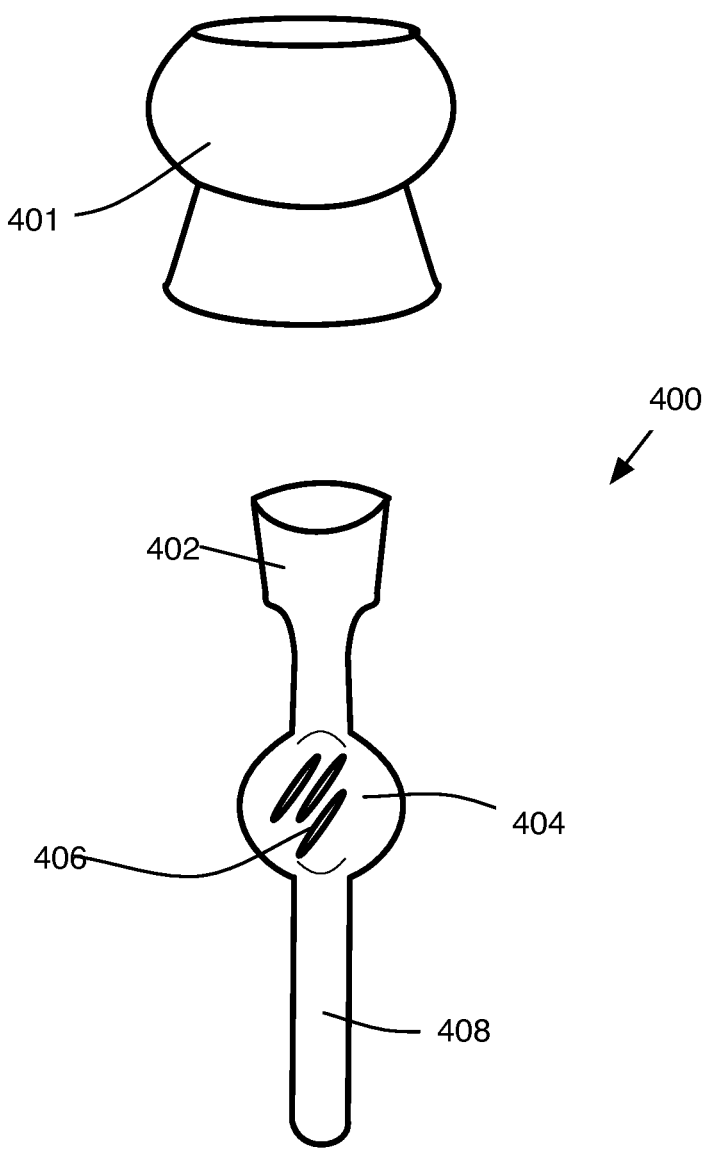
FIG. 4 is an exploded front view of a vapor cup insert according to one embodiment of the present invention.

FIG. 4 shows an alternate vapor cup insert 400 for vaporizing essential oils. It fits over a standard glassware tapered inlet, or in the inlet chamber 34 (of FIGS. 1 and 2, for example). The vapor cup includes an oil-receiving chamber 402, a sphere 404 having saw cuts 406 and a lower shaft portion 408. The vapor cup is well suited to filter vapors from volatized essential oils. The vapor cup is made from a quartz tubing adapted to fit on top of a $19/26$ inner joint. In use, the quartz vapor cup is preheated to a high temperature, this temperature would damage Pyrex glass. A blown sphere beneath the vapor cup's oil receiving chamber provides adequate clearance to avoid thermal damage to the glassware in which the insert is contacting or placed. The vapor cup is capped by a standard chimney 401.

Although the invention has been particularly shown and described with reference to certain embodiments, it will be understood by those skilled in the art that various changes in form and detail may be made without departing from the spirit and scope of the invention.

I claim:

1. A method of scrubbing a gas comprising:
providing a laboratory glass vessel comprising
an inlet chamber having an open top, the inlet chamber supporting a porous, incombustible pre-filter, the pre-filter comprising a first fritted disc arranged at a first height, the inlet chamber coupled to a downward extending conduit;
an exhaust chamber defined by at least one sidewall coupled to a bottom wall and the at least one sidewall defining an open top, the exhaust chamber further comprising a second fritted disc arranged at a second height, the exhaust chamber further comprising an inlet aperture located adjacent to the bottom wall and coupling to the downward extending conduit of the inlet chamber;
filling the exhaust chamber with a liquid to a liquid level-height such that the second fritted disc is covered by the liquid but the first pre-filter is not covered by the liquid;
providing a pressure differential across the vessel so that effluent gas at the exhaust chamber is at a lower pressure than incoming gas at the inlet chamber;
providing a sample;
heating or igniting the sample to create a gas having volatile solids; passing the gas through the first fritted disc, the second fritted disc, and the liquid comprising a volume of water contained in the exhaust chamber to scrub the gas of volatile solids of a size corresponding at least no larger than an aperture size of the second fritted disc.

* * * * *